(12) United States Patent
Ducauchuis et al.

(10) Patent No.: US 9,788,614 B2
(45) Date of Patent: Oct. 17, 2017

(54) FEMALE LOOP PORTION HAVING FILM AND FILAMENTS ANCHORED BY HEAT-SHRINKING

(75) Inventors: Jean-Pierre Ducauchuis, Nantes (FR); Anthony Mahe, St Julien de Concelles (FR)

(73) Assignee: APLIX, Paris (FR)

( * ) Notice: Subject to any disclaimer, the term of this patent is extended or adjusted under 35 U.S.C. 154(b) by 978 days.

(21) Appl. No.: 13/510,839

(22) PCT Filed: Nov. 10, 2010

(86) PCT No.: PCT/FR2010/000750
§ 371 (c)(1),
(2), (4) Date: Jun. 1, 2012

(87) PCT Pub. No.: WO2011/061416
PCT Pub. Date: May 26, 2011

(65) Prior Publication Data
US 2012/0231208 A1    Sep. 13, 2012

(30) Foreign Application Priority Data

Nov. 20, 2009  (FR) .................................. 09 05588

(51) Int. Cl.
*A44B 18/00* (2006.01)
*B32B 3/06* (2006.01)
(Continued)

(52) U.S. Cl.
CPC ...... *A44B 18/0011* (2013.01); *A44B 18/0069* (2013.01); *A61F 13/627* (2013.01); *B29C 47/0021* (2013.01); *B29C 55/06* (2013.01); *B29C 65/18* (2013.01); *B29C 66/034* (2013.01); *B29C 66/21* (2013.01); *B29C 66/474* (2013.01); *B29C 66/69* (2013.01); *B29C 66/73711* (2013.01); *B29C 66/73713* (2013.01);
(Continued)

(58) Field of Classification Search
CPC ... A44B 18/0011; A44B 18/0069; B32B 3/06; B32B 3/10; B32B 3/263; Y10T 428/23957; Y10T 428/23971; Y10T 428/24008; A61F 13/627
USPC ................................................ 428/99, 92, 94
See application file for complete search history.

(56) References Cited

U.S. PATENT DOCUMENTS 5,032,122 A * 7/1991 Noel et al. ................ 604/391
5,611,791 A    3/1997 Gorman et al.
(Continued)

FOREIGN PATENT DOCUMENTS

EP    0 289 198 A1    11/1988

*Primary Examiner* — Cheryl Juska
(74) *Attorney, Agent, or Firm* — Renner, Kenner, Greive, Bobak, Taylor & Weber (57) ABSTRACT

A female loop portion for a hook and loop self-adhesive, comprising a film (1) made of at least one thermoplastic and a plurality of filaments (2) which are separate from one another and attached to one of the surfaces of the film, each filament comprising a series of fastening sections (15) and a series of loop sections (4) alternating with the fastening sections, the filaments being attached to the film along the fastening sections while the loop sections are at a distance from the film so as to form loops, and characterized in that a cross-sectional area of one loop section of a filament is less than a cross-sectional area of one fastening section of said one filament.

11 Claims, 5 Drawing Sheets

(51) Int. Cl.
  B29C 55/06    (2006.01)
  B29C 65/18    (2006.01)
  B29C 65/00    (2006.01)
  A61F 13/62    (2006.01)
  B29C 35/08        (2006.01)
  B29C 47/00        (2006.01)
  B29C 47/30        (2006.01)
  B29C 59/14        (2006.01)
  B29C 61/02        (2006.01)
  B29C 35/04        (2006.01)
  B29K 23/00        (2006.01)
  B29K 101/12       (2006.01)
  B29L 9/00         (2006.01)
  B29L 31/48        (2006.01)

(52) U.S. Cl.
  CPC .. *B29C 66/73715* (2013.01); *B29C 66/81427* (2013.01); *B29C 66/81433* (2013.01); *B29C 66/83413* (2013.01); *B29C 66/83511* (2013.01); *B29C 66/9192* (2013.01); *B29C 66/91421* (2013.01); *B29C 66/91645* (2013.01); *B29C 66/93451* (2013.01); *B29C 35/08* (2013.01); *B29C 47/0014* (2013.01); *B29C 47/30* (2013.01); *B29C 59/14* (2013.01); *B29C 61/02* (2013.01); *B29C 66/71* (2013.01); *B29C 66/7371* (2013.01); *B29C 66/919* (2013.01); *B29C 66/91921* (2013.01); *B29C 66/91935* (2013.01); *B29C 66/939* (2013.01); *B29C 66/93441* (2013.01); *B29C 2035/046* (2013.01); *B29C 2035/0822* (2013.01); *B29C 2035/0838* (2013.01); *B29K 2023/0633* (2013.01); *B29K 2023/12* (2013.01); *B29K 2101/12* (2013.01); *B29K 2995/005* (2013.01); *B29K 2995/0049* (2013.01); *B29L 2009/00* (2013.01); *B29L 2031/4878* (2013.01); *Y10T 428/24008* (2015.01)

(56) References Cited

U.S. PATENT DOCUMENTS

| | | | | |
|---|---|---|---|---|
| 5,981,027 | A * | 11/1999 | Parellada | 428/120 |
| 6,733,610 | B2 * | 5/2004 | Mizutani et al. | 156/164 |
| 6,756,327 | B2 * | 6/2004 | Martin | 442/100 |
| 7,727,611 | B2 * | 6/2010 | Ducauchuis | 428/92 |
| 2007/0233023 | A1 | 10/2007 | Ducauchuis | |

* cited by examiner

FEMALE LOOP PORTION HAVING FILM AND FILAMENTS ANCHORED BY HEAT-SHRINKING

The present invention relates to a female loop portion for a hook and loop fastening device, in particular for use for fastening nappies, this female portion being intended in particular to be fixed to the waistband of the nappy centrally in the zone of the lower abdomen of the wearer of the nappy, commonly called Landing Zone.

The present invention also relates to a method for producing a female loop portion of this kind, and also to an installation for implementing a method of this kind.

Already known in the prior art is a female portion comprising a film made of thermoplastic material on which individual filaments have been anchored along anchoring sections in order to form loops with the parts of the filaments remaining unanchored. Reference may be made in particular to the French patent published under number 2 870 436 which is in the name of the applicant.

It would be desirable to obtain a female loop portion of the kind of the prior art described above which has filaments which are fixed to the film made of thermoplastic material as well as in the prior art and which moreover better withstand the tension, in particular when the loops cooperate with hooks.

According to a first aspect of the invention, a method for producing a fastener female portion, comprising a film made of one or more thermoplastic material(s) and filaments made of one or more thermoplastic material(s) fixed on one of the surfaces of the film in order to form loops, is characterised in that it comprises the steps which consist:

in taking a heat-shrinkable film consisting of one or more thermoplastic material(s), in depositing on the film a bundle or assembly of filaments consisting of one or more thermoplastic material(s) and not connected to one another, the material(s) of the film and the material(s) of the filaments being chosen so that the film is more heat-shrinkable than the filaments and in particular is heat-shrinkable whereas the filaments are substantially not, in performing a prefixing along each filament on a series of prefixing sections alternating with a series of free sections in which the filament is not fixed to the thermoplastic film, this prefixing being performed so that the materials of the filaments and of the film are not intimately connected; and in subjecting the assembly of film and prefixed filaments to a heat treatment causing the shrinking of the film and the softening of the filaments in order to obtain the female loop portion, the heat treatment being performed by heating to a temperature which is substantially equal to or greater than the Vicat A Point of the material or of at least one of the materials constituting the filaments and the Vicat A Point of the material or of at least one of the materials constituting the film and which is less than at least one of the melting points of the materials of the filaments and the film.

By thus providing for prefixing the filaments while at the same time preserving their integrity with respect to the film so that the materials are not intimately connected, in particular to an extent such that they are fixed to the film but may be easily detached therefrom while preserving if not their initial shape (generally the cross-section has been deformed) at least their integrity, then performing a heat-shrinking at a temperature which is greater than the softening temperatures of the filaments and of the film but less than the melting points of both, a shrinking of the material of the film and a particularly strong connection in the zones of prefixing of the filaments to the film material are obtained, without either the bases of the loops or the film made of thermoplastic material being degraded.

In the prior art, the methods for anchoring the filaments to the thermoplastic material of the film consisted mainly in welding or calendering which degraded the filaments particularly at the feet of the loops, tending to make them thinner. Moreover, these treatments tended to degrade the film to the point of piercing it, which required films of great thicknesses to be provided. By contrast, according to the invention, a higher tensile strength of the loops is obtained. Furthermore, at the end of the treatment the film does not become thinner, or at least becomes less thinner than in the prior art, compared with its thickness before the heat treatment, so that it is possible to provide for use from the start of thinner films than in the prior art or films as thin as in the prior art without fearing piercing of the film.

According to a preferred embodiment, the heat-shrinkable nature of the film is obtained by stretching it, in particular by a so-called "short" stretching, before depositing the bundle or assembly of filaments.

Preferably, the prefixing is carried out by a step in which the prefixing sections of the filaments are pressed against the film, while at the same time, the loop sections of the filaments are not pressed against the film.

In particular, the pressing is carried out by an engraved cylinder comprising raised zones corresponding to the zones intended for pressing the prefixing sections when the film and the filaments are sandwiched between the engraved cylinder and an opposed supporting surface which may in particular consist of a cylinder, which may be also engraved.

Preferably, the engraved pressing cylinder is heated, in particular to a temperature greater than the deformation temperature of the polymers employed but nevertheless below the Vicat A Points of the materials of the film and the filaments.

According to a second aspect of the invention, independent of the first aspect described above, and forming an invention in itself but which may be implemented in combination with the first aspect to improve it, the filaments of the bundle or assembly of filaments are produced directly by extrusion, before deposition on the film made of thermoplastic material.

According to a third aspect of the invention, independent of the first and second aspects, and forming an invention in itself but which may also be implemented in combination with either one of the first and second aspects or with both at the same time so as to improve them, the filaments are produced from POY (Pre Oriented Yarn) or LOY (Low Oriented Yarn).

POY is a yarn or filament made of a material conventionally used in spinning, for example a thermoplastic material such as polyester, but which during its production has not undergone all of the drawing steps, as described in numerous American patents, for example U.S. Pat. Nos. 4,736,500, 4,244,174 or 4,415,521.

According to a fourth aspect of the invention, independent of the other aspects, and forming an invention in itself but which may also be implemented in combination with any one or more than one of the other aspects so as to improve them, the prefixing sections are mutually offset between two successive filaments in the longitudinal direction of the filaments.

By thus providing an offset of the prefixing sections from one filament to the next in the succession of filaments of the bundle of filaments in the longitudinal direction in which the filaments extend, the final orientation of the loops formed by the loop sections in the final product, after the heat treatment, is influenced. Specifically, depending on this offset of the prefixing sections, the loops will tend to be oriented towards the left or towards the right relative to the longitudinal direction in which the filaments extend.

The present invention also relates to a female loop portion which can be obtained by one of the methods according to the invention.

According to a fifth aspect of the invention, independent of the other aspects, and forming an invention in itself but which may also be implemented in combination with any one or more than one of the other aspects so as to improve them, a female loop portion for a hook and loop fastener, comprising a film made of at least one thermoplastic material and a plurality of filaments, independent from one another and fixed to one of the surfaces of the film, each filament comprising a succession of fixing sections and a succession of loop sections alternating with the fixing sections, the filaments being fixed to the film along the fixing sections, while the loop sections are at a distance from the film in order to form loops, is characterised in that a cross-sectional area of a loop section of one filament is less than a cross-sectional area of a fixing section of said one filament.

Preferably, the largest of the cross-sectional areas of a loop section is less than the smallest of the cross-sectional areas of a fixing section.

Preferably, a bulb-shaped section extends between a loop section and a fixing section, the bulb-shaped section widening from the loop section towards the fixing section.

Preferably, the cross-sectional area of a loop section is constant, in particular being of circular shape.

Preferably, the cross-sectional area of a fixing section is constant, in particular being of oblong, for example elliptical or oval, shape.

According to a sixth aspect, independent of the other aspects, and forming an invention in itself but which may also be implemented in combination with any one or more than one of the other aspects so as to improve them, the filaments are made of POY or LOY.

According to a seventh aspect of the invention, independent of the other aspects and forming an invention in itself but which may also be implemented in combination with any one or more than one of the other aspects so as to improve them, the fixing sections are mutually offset in the longitudinal direction between two successive filaments.

Preferably, the filaments extend parallel to one another.

Preferably, the fixing sections of the filaments extend parallel at a distance between centres from one to the other which is between 0.02 mm and 0.5 mm, preferably between 0.05 mm and 0.15 mm, and in particular greater than 0.1 mm.

Preferably, the length over which each fixing section extends is between 0.1 mm and 1 mm, for example and preferentially 0.25 mm, while the length of each section forming the loops is between 0.5 mm and 5 mm, for example and preferentially 1 mm.

According to a preferred embodiment of the invention, the filaments have a count of between 5 and 15 Dtex, in particular equal to 8 Dtex. In particular, the count corresponds to the count of the filaments in the region of the loop sections (in particular excluding the bulb), knowing that the fixing sections have a count which is greater, since they have been "swollen" owing to the method according to the invention.

Preferably, seen in plan, the fixing section has a greater width, or transverse dimension perpendicularly to the longitudinal direction in which the filament extends, which is greater than the width of the loop section of the filament.

According to the invention, independent from one another is understood to mean filament loop sections which are not connected to their neighbours (for example as would be the case if they formed a sheet). The loop sections are connected to each other solely by the film made of plastic material but not directly to each other, even though it may arise that certain loop sections come into contact with others. However, although there may be contact between them, there is no fixing in the region of these contacts and the loop sections can be separated from one another.

According to an eighth aspect of the invention, independent of the other aspects and forming an invention in itself but which may also be implemented in combination with any one or more than one of the other aspects so as to improve them, the present invention also relates to an installation intended for producing a female loop element which comprises means for bringing a bundle of filaments and a film made of thermoplastic material into mutual contact in a gap between a pressing surface, in particular the surface of a pressing cylinder, and a supporting surface, in particular the surface of a supporting cylinder, the installation being characterised in that the pressing surface is engraved so as to form thereon raised zones intended to press selectively sections of the filaments against the film, while in the region of the non-raised portions of the pressing surface, sections of the filaments are not pressed against the film.

Preferably, there is provided, downstream of the pressing cylinder, a heating station intended to heat the film-filament assembly exiting from the gap.

Merely by way of illustration, embodiments of the different aspects of the invention will now be described with reference to the drawings in which.

Figure 1:
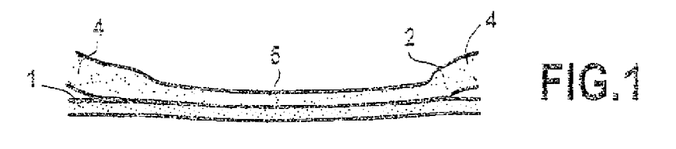
FIG. 1 shows, in longitudinal section, the state of a portion of a loop element during its production, after the prefixing step.
Figures 12, 13:
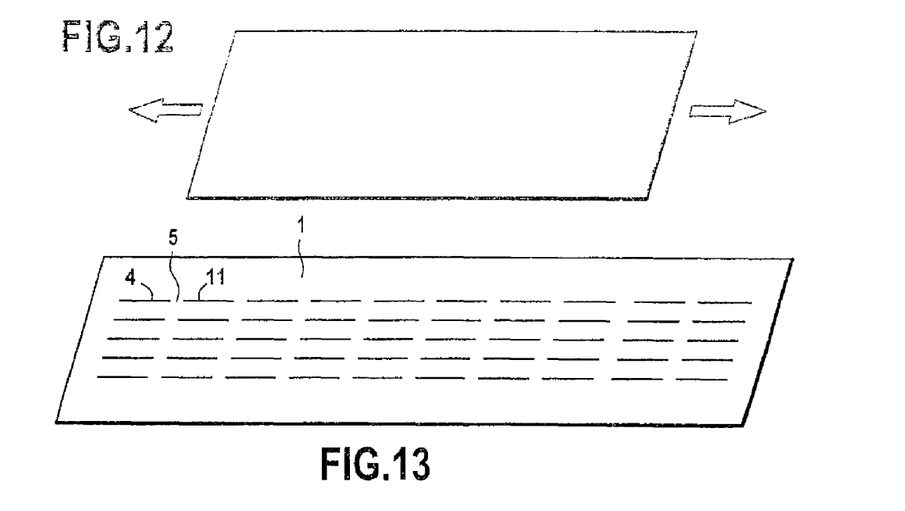
FIGS. 12 to 14 schematically represent a loop element during different production steps, FIG. 12 showing the film on its own before filaments have been extruded onto the film, FIG. 13 showing the state of the female element once the filaments have been positioned on the film and prefixed, and FIG. 14 showing the loop element obtained at the end of the method.
Figure 14:
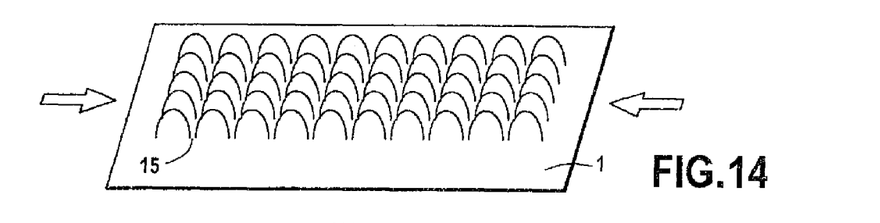

In FIG. 1, the loop element comprises a film 1 made of thermoplastic material on which have been deposited filaments 2 which extend parallel to one another in a longitudinal direction (from right to left in the figures). For a general view of this element, reference may be made in particular to FIG. 13 (corresponding to the state of FIG. 1) and to FIG. 14 (corresponding to the state of FIG. 2). Once the filaments have been positioned on the film 1, a prefixing along prefixing sections 5 is performed. Thus, along each filament there extend successively unfixed sections 4 intended to form a loop and prefixed sections 5. The fixed sections 5 are here in the form of straight-line segments.

Figure 2:
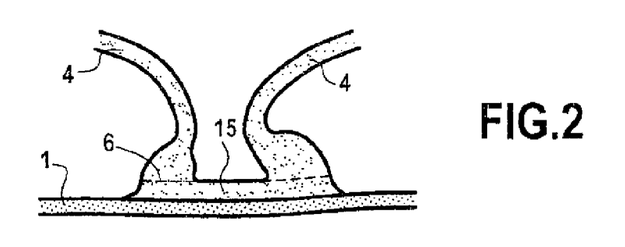
FIG. 2 shows, in longitudinal section, the same portion of the element of FIG. 1 as obtained at the end of the production method.
Figure 3:
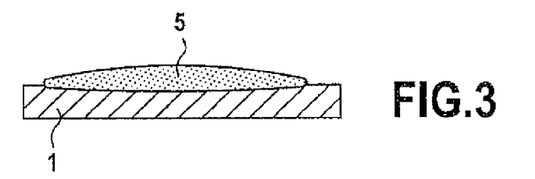
FIG. 3 shows schematically in cross-section the portion of the element of FIG. 17 along the line AA.

Once the prefixing of the filaments on the thermoplastic film has been carried out, there is performed a heat treatment which has the effect, on the one hand, of shrinking the film 1 and, on the other hand, of simultaneously softening the filaments in the prefixing sections 5. This results in very strong fixing of the filaments to the film in the region of fixing sections 15 (these fixing sections 15 correspond to the prefixing sections 5, but do not have the same dimensions as them, in particular length, owing to the shrinkage associated with the heat treatment). Furthermore, bulbs 6 form in the region of the feet of free sections 4, between each fixing section 15 and the following free section 4.

Figure 15:
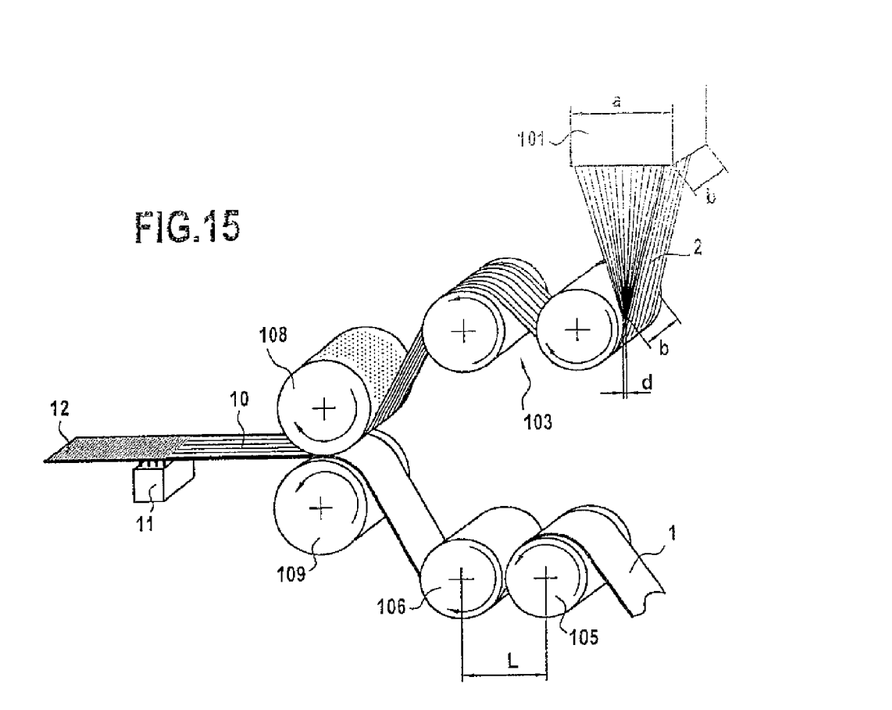
FIG. 15 shows an installation for producing a loop element according to the invention.

In FIG. 15, a device for producing a loop element is shown.

The die 101 makes it possible to extrude a multitude of filaments 2. The extrusion holes for the filaments are arranged so as to obtain a bundle of filaments of dimension a×b at the die outlet. The dimension of this bundle becomes d×b on arrival at the capstan 103, with d=diameter of the filaments. The arrangement of the holes in the die makes it possible to obtain filaments positioned at regular intervals beside one another on arrival at the capstan 103. The capstan 103 also makes it possible to cool the filaments. In this region, the filaments have a count of 1 to 22 dtex, preferably 8 to 9 dtex.

The film 1 arrives on the cylinder 105. Its thickness is, for example, 20 μm, preferably from 15 to 25 μm. It may also be between 10 and 100 μm. The cylinder 105 rotates at a speed V, for example 100 m/min. It is heated to a temperature generally equal to or greater than the Vicat Point of the film, for example 115° C. A small clearance is present between the two cylinders 105 and 106, this clearance is generally between 10 and 100 μm, depending on the film used. For example, for a film 1 of 20 μm, the gap will be 20 μm.

The cylinder 106 rotates at a speed V' greater than V in the opposite direction. for example, V'=2×V, i.e. 200 m/min. The film 1 is then stretched. The cylinder 106 is cooled between 15 and 25° C., allowing the film to be fixed in its stretched state.

The thickness of the film, once stretched, changes, according to the example, to a thickness equal to half the initial thickness, here 10 μm. The film is then fed to the positioning and prefixing module.

Figure 16:
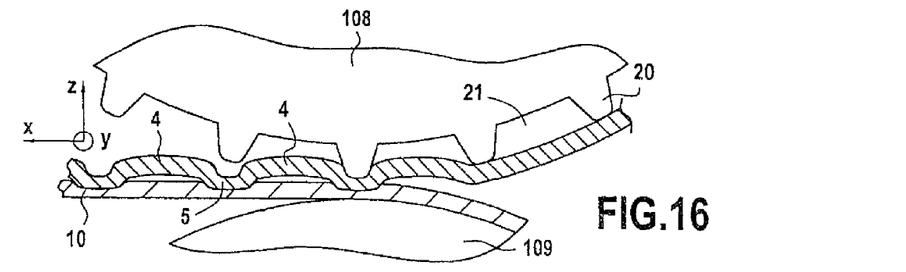
FIG. 16 is a side view of a part of the installation of FIG. 15 in the region where the prefixing of the filaments to the film is carried out.
Figure 17:
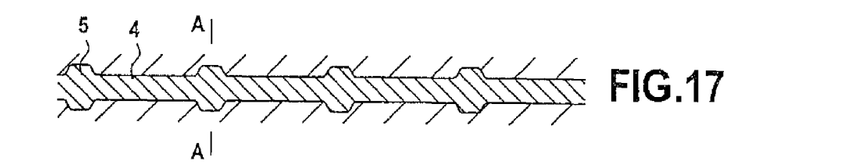
FIG. 17 is a plan view of a portion of a loop element once the prefixing has been performed and before the heat-treatment step.

The filaments 2 are positioned on the film with the aid of an engraved pressing cylinder 108 and a smooth supporting cylinder 109. These two cylinders apply a pressure to the product. The first objective of this step is to bring the filaments and the film into contact. The filaments and the film are brought into contact in distinct zones corresponding to the prefixing sections. To maintain this positioning despite the passing of the product through the machine, it is necessary to prevent the filament and the film from moving relative to one another. The step of positioning the filaments will therefore require compressing the two elements against one another, so as to create complementary shapes. This operation may be likened to a mechanical pre-anchoring of the two elements. This anchoring is insufficient to create a connection in the direction of the depth of the film but is sufficient to maintain the filaments on the film in the surface plane. To bring the film and the filaments into contact in specific zones and give them complementary shapes, two cylinders 108 and 109 are used. Engravings are made in the cylinder 108 so as to form raised zones 20. The two cylinders are pressed against one another, thus compressing the product passing between them at the raised zones 20 to form the prefixing sections 5. The pressure is only applied at the raised zones 20. In particular, at the intermediate zones 21 between two raised zones, the filaments and the film are not pressed against one another. In this way, the loop sections 4 are formed. To facilitate the deformation of the products, the two cylinders 108, 109 are heated. The temperatures are higher than the temperatures at which the polymers deform under load (Heat Deflection Temperature).

On the side of the film, the temperature of the cylinder must be lower than the heat-shrinking temperature of the film, 100° C. in the example.

The prepositioning and prefixing of the filaments on the film are carried out such that the connection between the filament and the film made of thermoplastic material remains superficial. Thus, the connection is made such that there is certainly contact but no interpenetration of the molecules constituting the filament and the film respectively. In particular, the filaments can be detached from the film without great difficulty. However, the filaments are deformed compared with their initial shape, in particular in the region of the sections 5 which have a more elongated oblong cross-section than the initial (generally circular) cross-section of the filaments.

The complex 10 formed by the film and the filaments on exiting from the cylinders 108, 109 is then heated by a heating device 11. This may, in particular, be a device for heating by hot air, or plasma, or radiation such as infrared radiation, or a laser, or any other energy supply means.

It is preferable for the heating device to be arranged on the side of the film opposite the filaments (as shown in FIG. 15). Thus, the heat firstly affects the film in order to heat-shrink it, while the filaments remain partly protected from the heat and only soften during the heat treatment.

This step makes it possible to shrink the film and soften the filaments in the region of the prefixing sections. A product is then obtained with loops which are intimately connected to the film and reinforced at their base.

For example, if the shrinking value is 2, the thickness of the bottom of the product becomes 20 μm again. If the entry speed of this step is 200 m/min, the product will then exit at 100 m/min.

Figure 7:
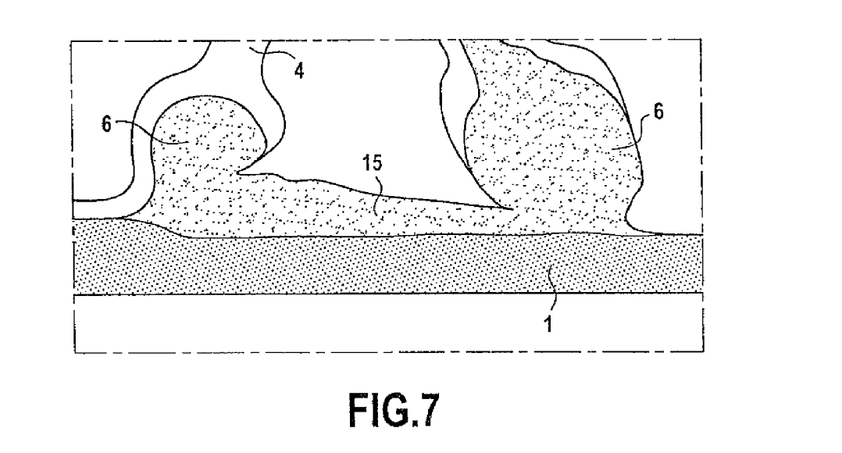
FIG. 7 is a perspective and sectional view on a larger scale of the element of FIG. 2.

The cross-sectional area (perpendicularly to the filament) of the filaments in the region of the loop sections 4, excluding the bulbs 6, is substantially equal to the cross-sectional area of the original filament. It is substantially constant from one bulb to the other. The bulbs 6 each extend from the substantially constant cross-section of the loops 4 as far as the fixing section 15. The two adjacent bulbs 6 are separated by a fixing section 15. The section 15 between the two bulbs has a substantially constant cross-sectional area. The cross-section of the section 15 between the two bulbs 6 is of flattened shape compared with that of the cross-sections of the loop-forming free sections 4. The cross-sectional area of the section 15 which extends between the two bulbs 6 is greater than the cross-sectional area of the sections 4, excluding the bulbs, and in particular the cross-section of the filament in the region of the crown (halfway between the two bulbs) of each loop 4. Furthermore, it is of flattened, in particular oval or slightly rectangular, shape.

Figure 6:
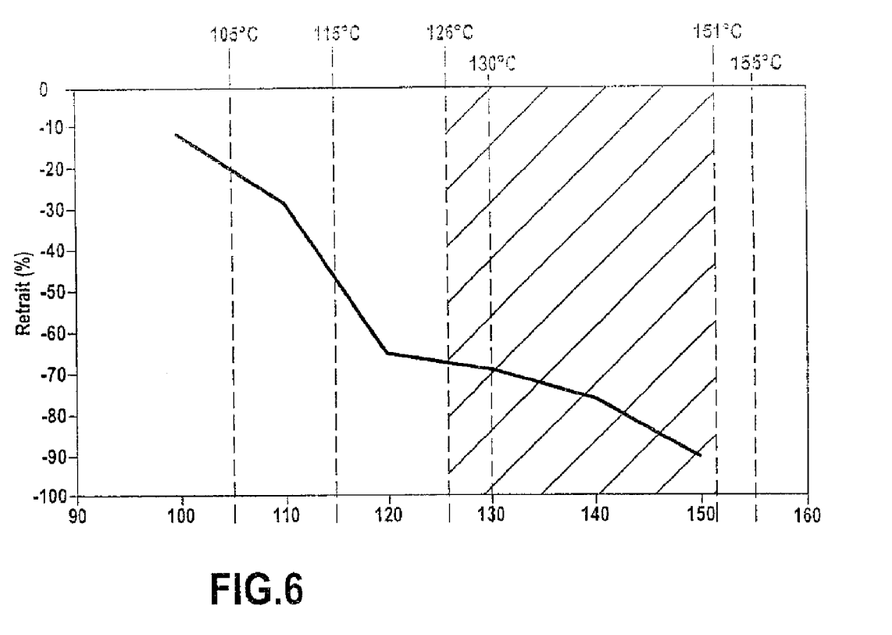
FIG. 6 is a graph showing the shrinkage of the film as a function of the heat-treatment temperature, the graph making it possible to define the optimum range (hatched) for the heat-treatment temperature according to the invention.

Thus, by providing a heat treatment in which the treatment temperature is higher than the Vicat Point of the materials of the film, and preferably also of the filaments, this ensures, with the concomitant heat-shrinking of the film, excellent fixing of the filaments. Furthermore, if a temperature higher than the Vicat temperature of the filaments is chosen, the softening of the filaments causes a deformation of the filaments and the formation in particular of the two bulbs 6 in the region of the feet of the loops which have the effect of improving the tensile and tear strength of these loops which thus have better resistance in their loop function in a hook and loop fastener. As shown in FIG. 6, the preferred working range is between the highest Vicat point among the Vicat Point of the filaments and the film and the lowest melting point of the melting points of the film and the filaments. FIG. 6 has been produced by way of example on the basis of a film made of LDPE and PP and filaments made of PP.

Figure 4:
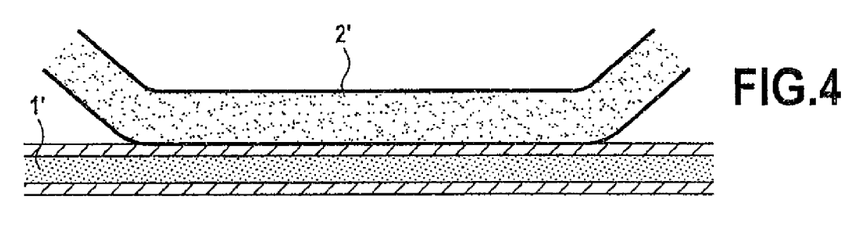
FIG. 4 is a schematic representation of another embodiment of an element according to the invention.

In FIG. 4, there is shown one possible exemplary embodiment for the chosen materials. The filaments 2' are made of polypropylene (PP), while the film 1' consists of a three-layer laminate comprising two outer layers of polypropylene (PP) and an inner layer made of low-density polyethylene (LDPE). Thus, the outer layers promote the intimate connection with the filaments, while the inner low-density polyethylene produces the heat-shrinking.

Figure 5:
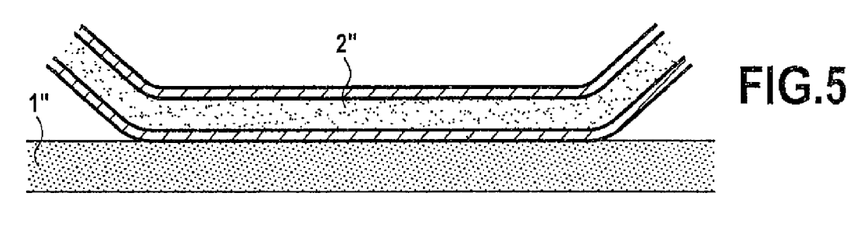
FIG. 5 is a view identical to FIG. 3 or 4 of still another embodiment of an element according to the invention.

Another possible embodiment consists in producing the film 1" from low-density polyethylene (LDPE) in its entirety (see FIG. 5), while the filaments 2" each consist of an outer sheath made of low-density polyethylene (LDPE) to promote the intimate connection with the film, and of a core made of polypropylene (PP) for their mechanical property.

Furthermore preferably, the filaments may be produced from POY, MOY or LOY. This has the advantage of increasing the peel or tensile strength when the female element is used with hooks. Furthermore, this improves the softness on contact with the skin, in particular, of babies.

The filaments of the LOY type are undrawn filaments or filaments of very low drawing. In spinning, these filaments are wound under the die at low speed, of the order of 500 to 600 m/min, without undergoing a drawing process. The filaments obtained thus have a large elongation capacity, generally greater than 195% of the initial length (initial length of 100%+elongation of 95%=195% of the initial length). The PP filaments used in the embodiments provided by way of example of the present invention may have an elongation of 500% of their initial length (the length of the filament after elongation then being 100+400=500% of the initial length).

The filaments of the POY (Partially Oriented Yarn) type are filaments of low drawing, of the order of a factor 2. The filament obtained then has an elongation less than the LOY but still greater than 160% (initial length of 100%+elongation of 60%=160% of the initial length)

Finally, there also exist intermediate filaments, called MOY, the elongation of which may reach 180%.

Figure 10:
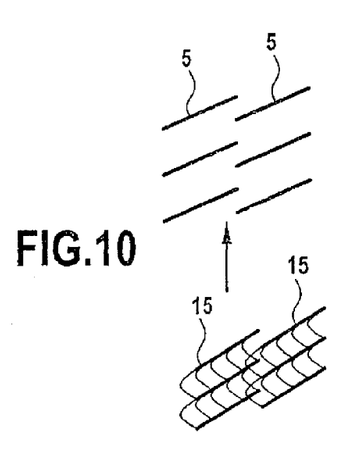
FIG. 10 is a diagram explaining a first method according to the invention for orienting the loops.
Figure 11:
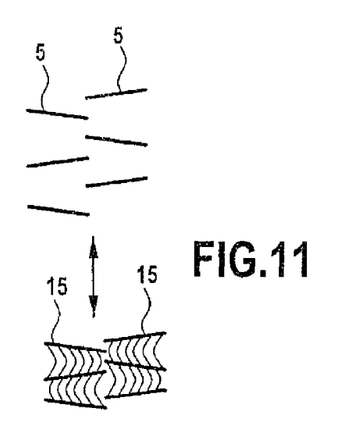
FIG. 11 is a diagram explaining a second method according to the invention for orienting the loops.

When performing the prefixing of the fixing sections, the prefixing sections may be offset relative to one another from one filament to another. Reference may thus be made to FIG. 10 or 11 in which there are shown patterns formed by the prefixing sections 5 after prefixing and the patterns formed by the fixing sections 15 after heat treatment. By thus arranging the prefixing sections offset transversely to the filaments, it is ensured, as shown, that the loops, after the heat treatment, will be oriented towards the left or the right, depending on the chosen pattern. When it is desired that the loop which extends between two consecutive fixing lines (the lines are in fact successions of sections 5 or 15 and these successions are schematically represented in the form of lines, even though strictly speaking they are not lines since there is discontinuity between two successive fixing sections in a line, the filaments being at a distance from one another) is oriented towards the left, the line is produced so as to increase from left to right (see FIG. 10 for a running direction towards the top of the figure).

If it is desired that the loops are oriented towards the right, the lines are produced, in a manner opposite to FIG. 10, so as to decrease from left to right.

It is also possible to produce any pattern comprising, as desired, loops oriented to the left and to the right, as in the example in FIG. 11 which is particularly advantageous in terms of peel strength.

Figure 8A:
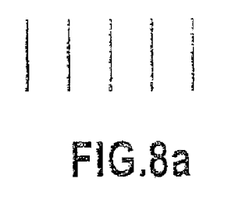
FIGS. 8A to 8C are plan views of different arrangement configurations of the loops.
Figure 8B:
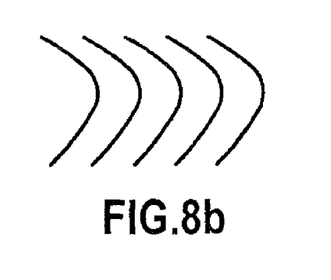
Figure 8C:
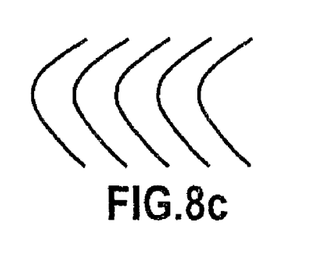
Figure 9A:
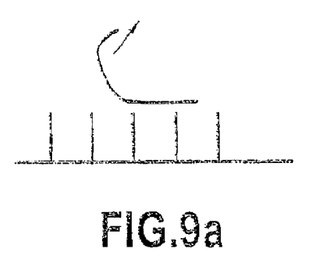
FIGS. 9A to 9C are side views of the arrangements of FIGS. 8A to 8C.
Figure 9B:
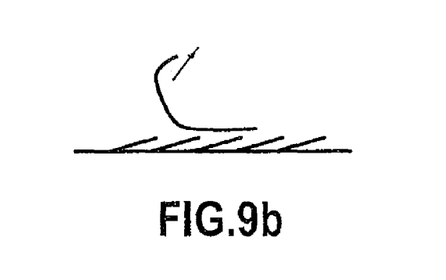
Figure 9C:
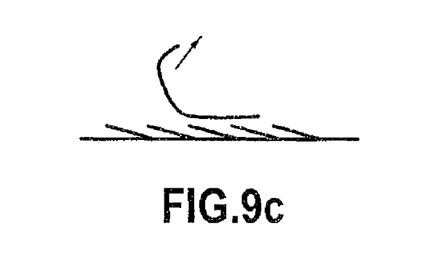
Figure 18:
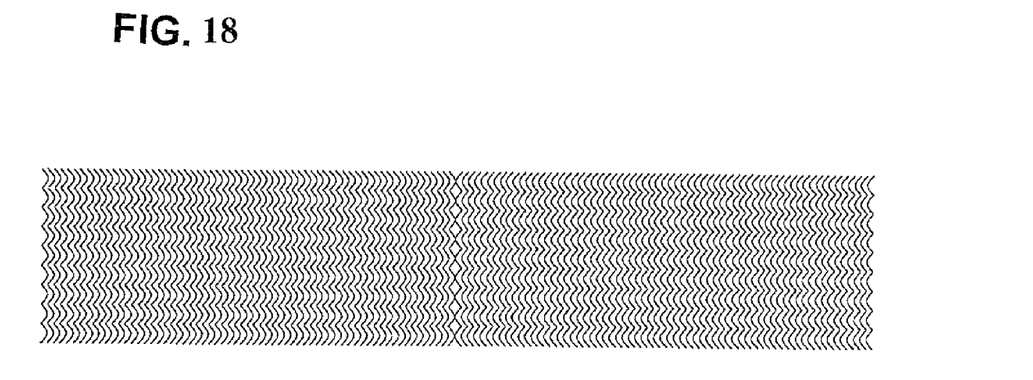
FIG. 18 shows in plan view a landing zone according to the invention comprising loops arranged according to a particularly advantageous pattern.

Thus, as shown in FIGS. 8c and 9c, the loops are oriented in the direction opposite the opening direction. This makes it possible to obtain peel forces greater than those of the configuration of FIGS. 8a and 9a and much greater than those of the configuration of FIGS. 8b and 9b. To obtain very high performance on a nappy landing zone, the arrangement shown in FIG. 18 is particularly advantageous. The loops there are oriented towards the left on the half of the landing zone which is to allow opening to the right and in the opposite direction for the left part. This arrangement of the loops could certainly also be obtained by using an orientation roller during and after the heat-shrinking. However, this latter method is not as precise as carrying out the orientation via the pattern itself as in accordance with the above-mentioned aspect of the invention.

It is, of course, possible to produce in a landing zone some loops towards the left and according to the opposite principle to produce other loops towards the right. It is also possible to produce loops which in a given filament are alternately oriented to the left and to the right as shown in FIG. 11.

According to the invention, the film has a thickness which is substantially constant situated in the region of the fixing sections or the loop sections, in particular, the thickness in the zone of the fixing sections is at most 25% lower than the thickness of the film outside these fixing zones and especially at most 20% lower, even more preferably at most 10% lower.

Preferably, the film is heat-shrinkable. Heat-shrinkable films are generally used in the field of packaging. The main application is the shrink-wrapping of a batch of products. Once bagged, the batch passes into an oven, the film shrinks and tightens over the products. This creates efficient packaging.

These films are generally bi-oriented, so as to be heat-shrinkable in all directions. To obtain such films, the initial film, generally based on ethylene, is stretched in both directions.

The film 1 obtained, see FIG. 1, is heat-shrinkable. It is sufficient subsequently to heat it to a temperature suitable for it to shrink. The method for obtaining this bi-orientation is to progressively increase the speeds of the drawing cylinders in MD and use a roller to stretch the film laterally.

Contrary to conventional heat-shrinkable films, the film used is preferably heat-shrinkable only in MD, in order to avoid waste in width and also perfectly control the density of filaments. The film will therefore be stretched in only one direction. To obtain a mono-oriented heat-shrinkable film, it has to be stretched only in one direction.

The product obtained is readily heat-shrinkable in MD but tends to swell in width under the effect of the temperature.

In FIG. 6, there is shown a graph giving the shrinkage of the film as a function of the heat-treatment temperature. This graph has been produced for a three-layer film of PP, LDPE and PP, while the filaments are made of PP. The melting point of the LDPE is 105° and the Vicat A point of the PP is 115° C., while the Vicat A point of the PP material of the filaments is 126° C.

A temperature of 130° C. is thus chosen for the heat treatment, which is higher than the above Vicat A points of the materials of the film and the filaments and lower than the melting temperature of the PP of the film (melting point of the PP is 151° C.) and of the filaments (155° C.).

In the present invention, heat-shrinkable is understood to mean an element, in particular a film, which shrinks by at least 10% (preferably by at least 20%) when it is heated to a temperature less than 10° from its melting point.

The invention claimed is:

1. A female loop portion for a hook and loop fastener, comprising a film made of at least one thermoplastic material and a plurality of filaments, independent from one another and fixed to one of the surfaces of the film, each filament comprising a succession of fixing sections and a succession of loop sections alternating with the fixing sections, the filaments being fixed to the film along the fixing sections so that said filaments in said fixing sections are in direct contact with said film, while the loop sections are at a distance from the film in order to form loops, so that said filaments in said fixing sections are at least in part outside said film and so that a cross-sectional area of a loop section of one filament is less than a cross-sectional area of a fixing section of said one filament.

2. A female loop portion according to claim 1, characterized in that the largest of the cross-sectional areas of a loop section is less than the smallest of the cross-sectional areas of a fixing section.

3. The female loop portion according to claim 1, characterized in that a bulb-shaped section extends between a loop section and a fixing section, the bulb-shaped section widening from the loop section towards the fixing section.

4. The female loop portion according to claim 1, characterized in that the cross-sectional area of a loop section is constant.

5. The female loop portion of claim 4, wherein the cross-sectional area of a loop section is circular in shape.

6. The female loop portion according to claim 1, characterized in that the cross-sectional area of a fixing section is constant.

7. The female loop portion of claim 6, wherein the cross-sectional area of a fixing section is oblong in shape.

8. The female loop portion according to claim 1, characterized in that the filaments are made of POY or LOY.

9. The female loop portion according to claim 1, characterized in that the fixing sections are mutually offset in the longitudinal direction between two successive filaments.

10. The female loop portion according to claim 1, characterized in that the filaments extend parallel to one another.

11. A female loop portion for a hook and loop fastener, comprising a film made of at least one thermoplastic material and a plurality of filaments, independent from one another and fixed to one of the surfaces of the film, each filament comprising a succession of fixing sections and a succession of loop sections alternating with the fixing sections, the filaments being fixed to the film along the fixing sections so that said filaments in said fixing sections are in direct contact with said film, while the loop sections are at a distance from the film in order to form loops, so that said filaments in said fixing sections are at least in part outside said film and so that a cross-sectional area of a loop section of one filament is less than a cross-sectional area of a fixing section of said one filament; and wherein measured in a direction perpendicular to said film a thickness of said film at the fixing sections is not smaller than a thickness of said film at said loop sections by more than 25%.

* * * * *